United States Patent
Yamashita et al.

(10) Patent No.: US 10,906,793 B2
(45) Date of Patent: Feb. 2, 2021

(54) CARBONATED DRINK FILLING METHOD AND CARBONATED DRINK FILLING SYSTEM

(71) Applicant: Dai Nippon Printing Co., Ltd., Tokyo (JP)

(72) Inventors: Toru Yamashita, Tokyo (JP); Atsushi Hayakawa, Tokyo (JP); Takuma Miyawaki, Tokyo (JP); Yusuke Suga, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 396 days.

(21) Appl. No.: 15/512,688

(22) PCT Filed: Sep. 18, 2015

(86) PCT No.: PCT/JP2015/076726
§ 371 (c)(1),
(2) Date: Mar. 20, 2017

(87) PCT Pub. No.: WO2016/047609
PCT Pub. Date: Mar. 31, 2016

(65) Prior Publication Data
US 2017/0297884 A1      Oct. 19, 2017

(30) Foreign Application Priority Data

Sep. 25, 2014   (JP) ................................. 2014-194747

(51) Int. Cl.
*B08B 9/32*      (2006.01)
*B29C 49/06*     (2006.01)
(Continued)

(52) U.S. Cl.
CPC ............... *B67C 3/22* (2013.01); *B08B 9/32* (2013.01); *B29C 49/06* (2013.01);
(Continued)

(58) Field of Classification Search
CPC ............ B29C 49/4273; B29C 49/64; B29C 2071/025; B29C 2049/4685;
(Continued)

(56) References Cited

U.S. PATENT DOCUMENTS 3,512,996 A * 5/1970 Roe, Jr. ................. B29C 49/68
                                                   264/348
5,073,182 A * 12/1991 Virey .................... C03B 9/3808
                                                   65/84
(Continued)

FOREIGN PATENT DOCUMENTS

DE   10 2008 048 812 A1   4/2010
FR      2 939 708 A1      6/2010
(Continued)

OTHER PUBLICATIONS

Extended European Search Report (Application No. 15844366.3) dated May 18, 2018.
(Continued)

*Primary Examiner* — Thanh K Truong
*Assistant Examiner* — Patrick B Fry
(74) *Attorney, Agent, or Firm* — Burr & Brown, PLLC (57) ABSTRACT

In a carbonated drink filling method, a preform is continuously transferred and introduced into a heating furnace, heated to a temperature for molding the preform into a container, molded into the container in a molding die after the preform exits the heating furnace, conveyed in an upright position during which a coolant (F) is injected to a bottom of the container to cool the bottom. The container is filled with a carbonated drink (a) through a mouth portion of the container, and the mouth portion is then sealed. The coolant is injected in the cooling to the bottom of the container from a nozzle opening on either or both sides of a conveyance line of the container, and the nozzle opening is directed diagonally upward to the bottom of the container in such a manner that an extension of the nozzle opening intersects with the conveyance line of the container.

4 Claims, 11 Drawing Sheets

(51) Int. Cl.
*B29C 49/42* (2006.01)
*B29C 49/64* (2006.01)
*B67C 3/22* (2006.01)
*B67C 7/00* (2006.01)
*B29K 67/00* (2006.01)
*B29K 105/00* (2006.01)
*B29L 31/00* (2006.01)

(52) U.S. Cl.
CPC ...... *B29C 49/4273* (2013.01); *B29C 49/6409* (2013.01); *B67C 7/00* (2013.01); *B67C 7/002* (2013.01); *B67C 7/0046* (2013.01); *B67C 7/0073* (2013.01); *B29K 2067/003* (2013.01); *B29K 2105/258* (2013.01); *B29L 2031/7158* (2013.01); *B67C 2003/227* (2013.01); *B67C 2003/228* (2013.01)

(58) Field of Classification Search
CPC . B29C 2049/4688; B67C 7/0073; B67C 7/00; B65B 2003/227; B65B 55/10
USPC ........ 53/452, 167, 281, 426, 471, 453, 558, 53/559; 264/348
See application file for complete search history.

(56) References Cited

U.S. PATENT DOCUMENTS

| | | | | |
|---|---|---|---|---|
| 6,475,422 | B1* | 11/2002 | Neter | B29C 35/16 264/328.14 |
| 7,632,089 | B2* | 12/2009 | Bates | B29C 43/08 425/534 |
| 7,887,319 | B2* | 2/2011 | Takatomi | B29C 49/6427 425/526 |
| 8,573,266 | B2* | 11/2013 | Knapp | B67C 3/045 141/11 |
| 8,650,908 | B2* | 2/2014 | Brown | C03B 27/06 65/114 |
| 9,545,746 | B2* | 1/2017 | Dachs | B29C 35/16 |
| 9,908,650 | B2* | 3/2018 | Sollner | B65B 55/10 |
| 2002/0076462 | A1 | 6/2002 | Boyd et al. | |
| 2007/0235906 | A1 | 10/2007 | Trouillet | |
| 2011/0154785 | A1 | 6/2011 | Stolte | |
| 2012/0085071 | A1 | 4/2012 | Hahn et al. | |
| 2013/0061557 | A1 | 3/2013 | Kitano et al. | |
| 2015/0225098 | A1* | 8/2015 | Sollner | B65B 55/10 53/426 |
| 2016/0002018 | A1* | 1/2016 | Clusserath | B65B 63/08 53/426 |

FOREIGN PATENT DOCUMENTS

| | | |
|---|---|---|
| JP | 2008-501558 A | 1/2008 |
| JP | 2010-202284 A | 9/2010 |
| JP | 2013-233979 A | 11/2013 |
| JP | 2013-237484 A | 11/2013 |
| WO | 2011/148953 A1 | 12/2011 |

OTHER PUBLICATIONS

International Search Report (With English Translation) and Written Opinion, International Application No. PCT/JP2015/076726, dated Dec. 22, 2015 (8 pages).

* cited by examiner

FIG.3

FIG.5(α) INJECTION OF HYDROGEN PEROXIDE FROM DIRECTLY ABOVE

FIG.5(β) AIR RINSING

FIG.8(D1) COOLING OF BOTTOM OF BOTTLE

FIG.8(β) AIR RINSING

FIG.8(α) INJECTION OF HYDROGEN PEROXIDE FROM DIRECTLY ABOVE

CARBONATED DRINK FILLING METHOD AND CARBONATED DRINK FILLING SYSTEM

TECHNICAL FIELD

The present invention relates to a carbonated drink filling method and a carbonated drink filling system.

BACKGROUND ART

According to prior art, a preform is continuously transferred and introduced into a heating furnace, heated in the heating furnace to a temperature for molding the preform into a bottle and molded into a bottle in a molding die after the preform exits the heating furnace. The bottle is then sterilized and inverted. Water is then injected into the bottle to wash the interior of the bottle and at the same time is injected to the bottom of the bottle to cool the bottom of the bottle. After that, the bottle is restored to the upright position and then is filled with a carbonated drink. According to this process, even if the bottle has a thick bottom, such as a pressure-resistant bottom, and it takes a long time for heat removal, the bottom of the bottle can be quickly cooled. Thus, even if the bottle is filled with a carbonated drink shortly after the molding of the bottle, the bottom of the bottle is not deformed, and thus the stability of the bottle can be improved (see Patent Literature 1, for example).

CITATION LIST

Patent Literature

Patent Literature 1: Japanese Patent Laid-Open No. 2013-237484

SUMMARY OF INVENTION

Technical Problem

According to the conventional technique described above, the bottle is transferred in the inverted position, and water is injected into the bottle for washing and at the same time is injected to the bottom of the bottle for cooling. Thus, the bottle molded in the upright position needs to be inverted and then restored to the upright position. This leads to an increase in complexity of the structure of the manufacturing line and an increase in equipment cost.

An object of the present invention is to solve the problem described above.

Solution to Problem

To solve the problem described above, the present invention is configured as described below.

In the description below, to facilitate understanding of the present invention, reference numerals are shown in parentheses. However, the present invention is not limited to the following description.

That is, the present invention according to a first aspect adopts a carbonated drink filling method, wherein a preform (1) is continuously transferred and is introduced into a heating furnace (33), the preform (1) is heated to a temperature for molding the preform into a container (2) in the heating furnace (33), the preform (1) is molded into the container (2) in a molding die (4) after the preform (1) exits the heating furnace (33), the container (2) is conveyed in an upright position, a coolant (F) is injected to a bottom (2b) of the container (2) to cool the bottom (2b) of the container (2), the container (2) is filled with a carbonated drink (a) through a mouth portion (2a) of the container (2), and the mouth portion (2a) is then sealed, the coolant (F) being injected in the cooling to the bottom (2b) of the container (2) from a nozzle opening on either or both sides of a conveyance line of the container (2), and the nozzle opening being directed diagonally upward to the bottom (2b) of the container (2) in such a manner that an extension of the nozzle opening intersects with the conveyance line of the container (2).

According to a second aspect of the present invention, in the carbonated drink filling method according to the first aspect, the container (2) may be subjected to a sterilization process before the container (2) is filled with the carbonated drink (a), and the bottom (2b) of the container (a) may be cooled before and/or after the sterilization process.

According to a third aspect of the present invention, in the carbonated drink filling method according to the first aspect, the container (2) may be subjected to a sterilization process before the container (2) is filled with the carbonated drink (a), the container (2) is subjected to water rinsing after the sterilization process, and the bottom (2b) of the container (2) may be cooled after the water rinsing.

That is, the present invention according to a fourth aspect adopts a carbonated drink filling system, comprising: a transfer device that transfers a preform (1) and a container (2) from where the preform (1) is supplied and molded into the container (2) to where the container (2) is filled with a carbonated drink (a) and sealed; a heating furnace (33) that heats the preform (1) to a molding temperature; a blow molding die (4) that blow-molds the preform (1) into the container (2); a coolant injection nozzle (28) that injects a coolant (F) to a bottom (2b) of the container (2) discharged from the blow molding die (4) in an upright position to cool the bottom (2b) of the container (2); a filler (39) that fills the container (2) with the carbonated drink (a) through a mouth portion (2a) of the container (2); and a capper (40) that seals the mouth portion (2a) of the container (2), the heating furnace (33), the blow molding die (4), the coolant injection nozzle (28), the filler (39) and the capper (40) being arranged in this order from an upstream side to a downstream side along the transfer device, the coolant injection nozzle (28) being provided on either or both sides of a conveyance line of the container (2), and the coolant (F) being injected from a nozzle opening that is directed diagonally upward to the bottom (2b) of the container (2) in such a manner that an extension of the nozzle opening intersects with the conveyance line of the container (2).

According to a fifth aspect of the present invention, in the carbonated drink filling system according to the fourth aspect, a sterilization device (30) that performs a sterilization process on the container (2) may be provided upstream of the filler (39), and the coolant injection nozzle (28) may be provided upstream and/or downstream of the sterilization device (30).

According to a sixth aspect of the present invention, in the carbonated drink filling system according to the fourth aspect, a sterilization device (30) that performs a sterilization process on the container (2) may be provided upstream of the filler (39), a water rinsing device may be provided downstream of the sterilization device (30), and the coolant injection nozzle (28) may be provided between the water rinsing device and the filler.

Advantageous Effects of Invention

According to the carbonated drink filling method according to the present invention, a preform (1) is continuously transferred and is introduced into a heating furnace (33), the preform (1) is heated to a temperature for molding the preform (1) into a container (2) in the heating furnace (33), the preform (1) is molded into the container (2) in a molding die (4) after the preform (1) exits the heating furnace (33), the container (2) is conveyed in an upright position, a coolant (f) is injected to a bottom (2b) of the container (2) to cool the bottom (2b) of the container (2), the container (2) is filled with a carbonated drink (a) through a mouth portion (2a) of the container (2), and the mouth portion (2a) is then sealed, the coolant (F) being injected in the cooling to the bottom (2b) of the container (2) from a nozzle opening on either or both sides of a conveyance line of the container (2), and the nozzle opening being directed diagonally upward to the bottom (2b) of the container (2) in such a manner that an extension of the nozzle opening intersects with the conveyance line of the container (2). Thus, while the container (2) having just been molded is being transferred in the upright position, the bottom (2b) of the container (2) can be quickly cooled to prevent sagging or other deformation thereof, and even if the container (2) is filled with the carbonated drink (a) shortly after the container (2) is molded, outward deformation of the bottom (2b) of the container (2) can be prevented, and the stability of the container (2) can be improved. In addition, unlike the conventional technique, there is no need to invert the container (2) molded in the upright position and then restore the container (2) to the upright position, and the container (2) can be kept in the upright position during transfer thereof, the structure of the manufacturing line of the bottled carbonated drink product can be simplified. In addition, when the bottom (2b) of the container (2) is cooled, the coolant (F) is injected to the bottom (2b) of the container (2) from a nozzle opening on either or both sides of a conveyance line of the container (2), and the nozzle opening is directed diagonally upward to the bottom (2b) of the container (2) in such a manner that an extension of the nozzle opening intersects with the conveyance line of the container (2). Thus, even if the coolant F is a liquid, such as water, droplets of the liquid are less likely to reach the mouth portion 2a of the bottle 2, so that the possibility that the droplets enter the bottle (2) to contaminate the interior of the bottle (2) is eliminated.

DETAILED DESCRIPTION OF THE INVENTION

In the following, embodiments of the present invention will be described.

First Embodiment

First, a carbonated drink filling method will be described.

Figure 1A:
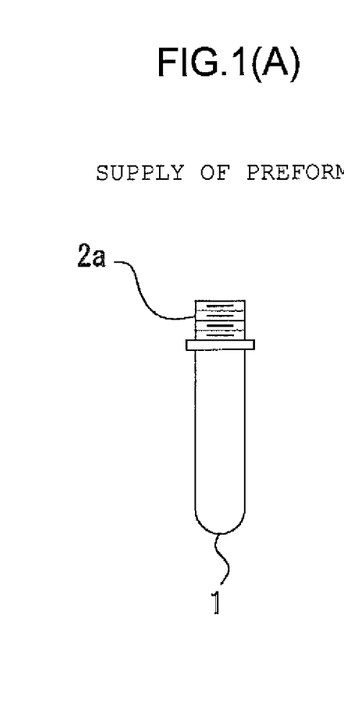
FIG. 1(A) shows a step in the first half of a carbonated drink filling method according to the present invention.

First, a preform 1 shown in FIG. 1(A) is continuously conveyed at a desired velocity.

Figure 2D:
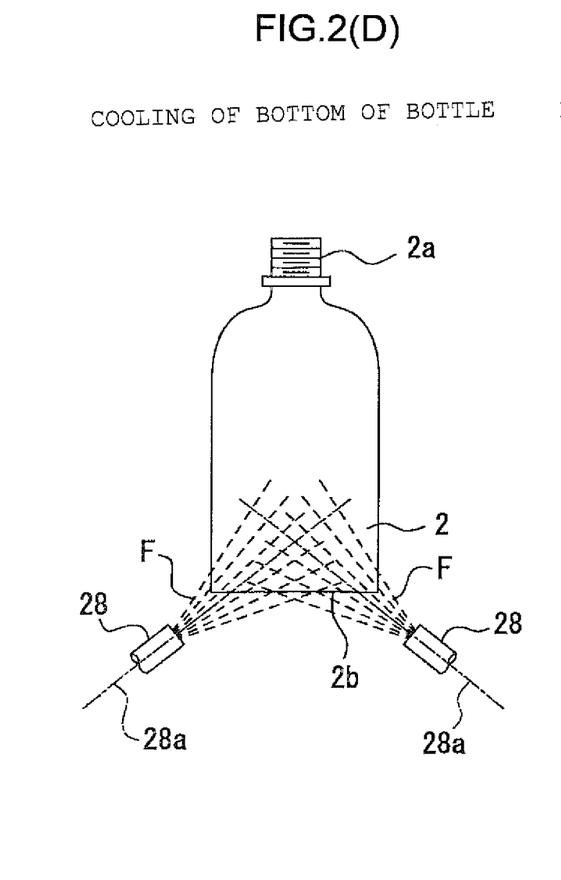
FIG. 2(D) shows a step in the second half of the carbonated drink filling method according to the present invention.
Figure 2E:
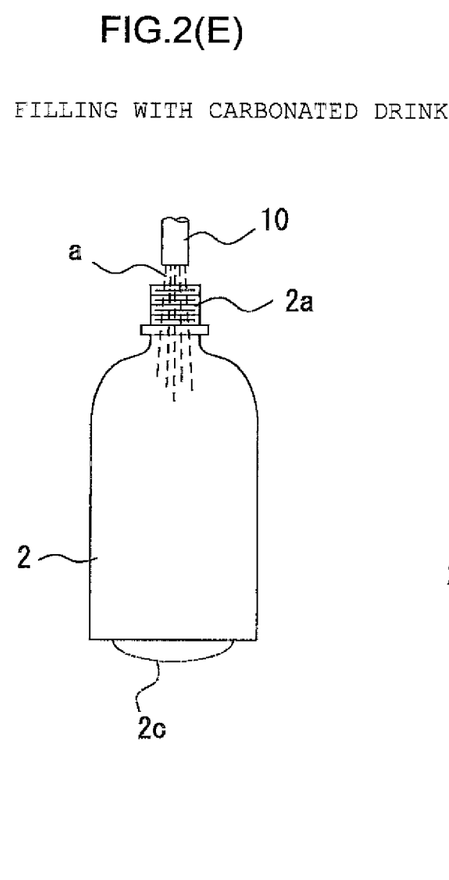
FIG. 2(E) shows a step in the second half of the carbonated drink filling method according to the present invention.
Figure 2F:
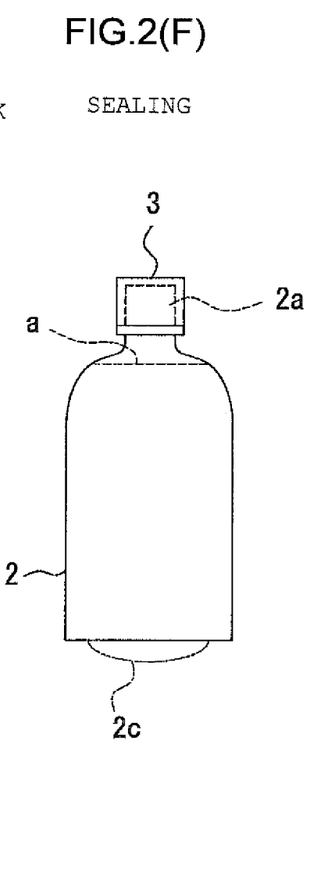
FIG. 2(F) shows a step in the second half of the carbonated drink filling method according to the present invention.

The preform 1 is a bottomed tubular body similar to a test tube that is previously formed from PET (polyethylene terephthalate) by injection molding or the like. A mouth portion 2a similar to that of a bottle 2 shown in FIGS. 2(D) to 2(F) is formed on the preform 1 in an early stage of the molding of the preform 1. A male thread corresponding to a female thread on a cap 3 is formed on the mouth portion 2a during the molding of the preform 1.

Figure 1B:
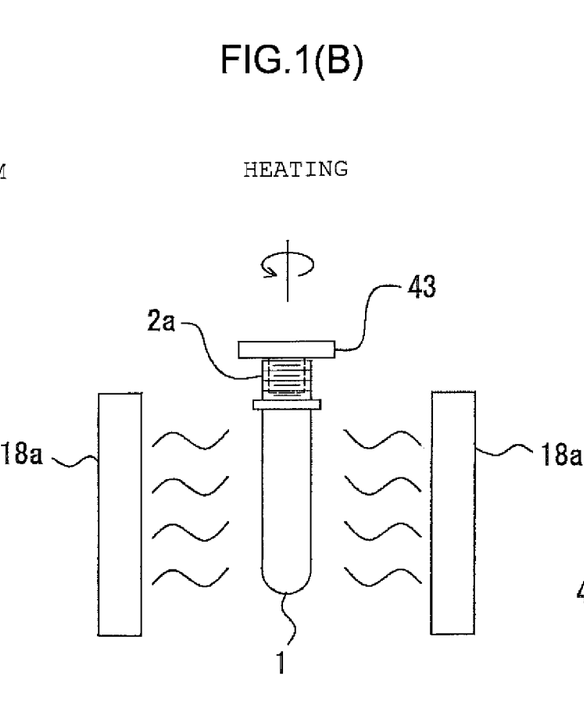
FIG. 1(B) shows a step in the first half of the carbonated drink filling method according to the present invention.

Next, as shown in FIG. 1(B), the preform 1 is heated to a temperature suitable for the subsequent blow molding by an infrared heater 18a or other heating device. The temperature is approximately between 90° C. and 130° C.

The temperature of the mouth portion 2a of the preform 1 is maintained to be equal to or lower than 70° C. to prevent deformation, for example.

In the heating, as shown in FIG. 1(B), the preform 1 is desirably suspended in an upright position (or inverted position) from a spindle (or mandrel) 43 inserted into the mouth portion 2a thereof and is conveyed while rotating with the spindle (or mandrel) 43. Thus, the preform 1 is uniformly heated by the infrared heater 18a.

If the mandrel is inserted into the preform 1 instead of the spindle 43, the preform 1 can be rotated and conveyed in the inverted position.

Figure 1C:
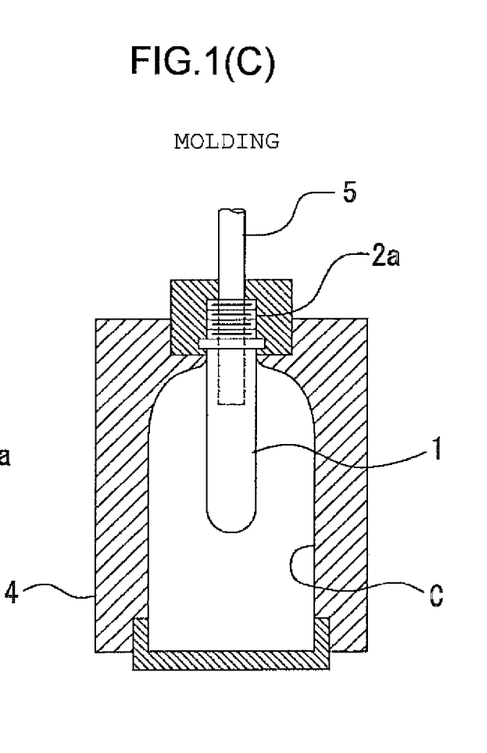
FIG. 1(C) shows a step in the first half of the carbonated drink filling method according to the present invention.

As shown in FIG. 1(C), the heated preform 1 is blow-molded into the bottle 2 in a die 4.

The die 4, which is a molding die for blow molding, is clamped while being continuously rotated at the same speed as the transfer speed of the preform 1 and is opened after the blow molding of the preform 1 in the die 4 is completed.

The preform 1 excluding the mouth portion 2a is uniformly heated to a temperature range suitable for molding in the heating step shown in FIG. 1(B) as described above, and the heated preform 1 is placed in the die 4, and an extension rod 5 is inserted in the preform 1 placed in the die 4 as shown in FIG. 1(C).

When the die 4 is being transferred, for example, primary blowing air and secondary blowing air are sequentially blasted into the preform 1 from an extension rod (not shown) to expand the preform 1 into the bottle 2 as a final molded product in a cavity C of the die 4.

Once the bottle 2 is molded in the die 4, the die 4 is opened while being continuously transferred, and the bottle 2 as a finished product is removed from the die 4 in the upright position.

The bottle just removed from the die 4 is hot and soft. In particular, a central portion of a bottom 2b of the bottle 2 is the thickest and thus takes some time to cool and set. If the bottle 2 that has not adequately cooled down is filled with a carbonated drink and sealed, a buckling 2c shown by the alternate long and two short dash lines in FIGS. 2(E) and 2(F) can occur on the bottom 2b of the bottle. The buckling 2c is a phenomenon in which the bottom 2b of the bottle 2 that is still soft sags down in a protrusion form under a counter pressure applied immediately before filling the bottle with the carbonated drink or the internal pressure of the carbonated drink or the like supplied into the bottle. In particular, if the bottle 2 is to be filled with a drink, such as the carbonated drink, that acts to increase the pressure in the bottle 2 after filling, the bottom 2b of the bottle 2 is made thicker than the other parts to form a petaloid bottom to resist the pressure and thus is less susceptible to cooling and setting, so that the buckling 2c is more likely to occur. If the bottle 2 sets while the buckling 2c is not eliminated, the resulting bottle 2 is unstable and can fall.

To prevent occurrence of the buckling 2c, as shown in FIG. 2(D), the bottom 2b of the bottle 2 is forcedly cooled by injecting a coolant F to the bottom 2b of the bottle 2 from outside the bottle 2.

The coolant F may be a gas, such as air, or a liquid, such as water. In the case of a filling machine that produces a product that requires sterilization, aseptic air, aseptic water, or a sterilizer containing a constituent such as peracetic acid, hydrogen peroxide, sodium hypochlorite, ozone water or acid water can be used as the coolant.

As a device for injecting the coolant F to the bottom 2b of the bottle 2, a coolant injection nozzle 28 shown in FIG. 2(D) is used.

Figure 4:
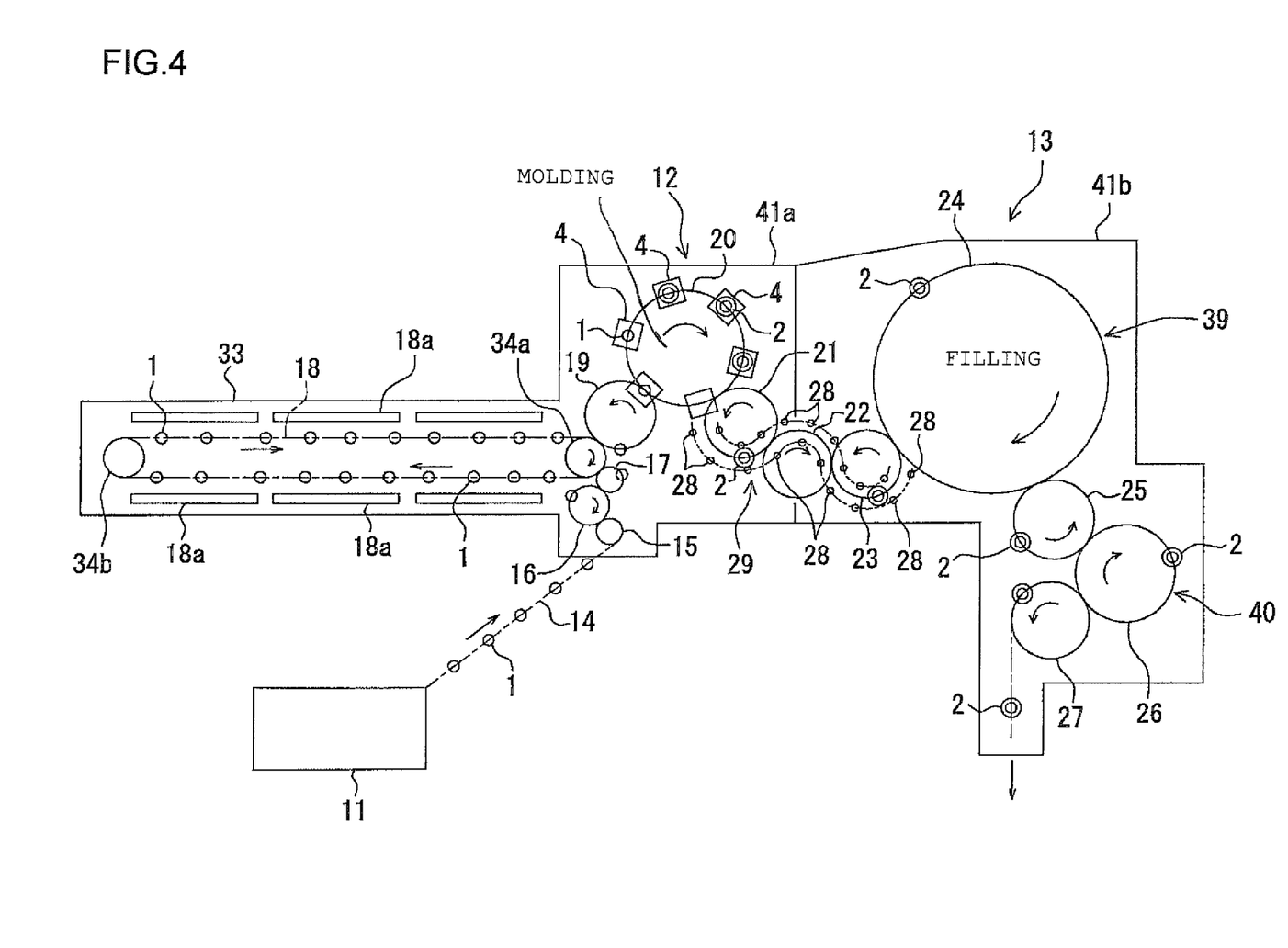
FIG. 4 is a schematic plan view of a carbonated drink filing system according to the present invention.

Coolant injection nozzles 28 are arranged on the opposite sides of the conveyance line of the bottle 2, and nozzle openings of the coolant injection nozzle 28 are directed diagonally upward to the bottom 2b of the bottle 2 in such a manner that the extensions of the nozzle openings intersect with the conveyance line of the bottle 2. In FIG. 2(D), an alternate long and short dash line 28a indicates the centerline of the nozzle opening. A large number of coolant injection nozzles 28 are arranged on the opposite sides of the bottle 2 being conveyed along the direction of conveyance of the bottle 2, as shown in FIG. 4. For example, the coolant injection nozzles are arranged in two rows in a staggered configuration. To address the difference in size in the lengthwise direction between bottles 2, the coolant injection nozzles may also be arranged in a plurality of rows in the vertical direction, as required.

Since the coolant F is injected from the coolant injection nozzles 28 to the bottom 2b of the bottle 2, the bottom 2b of the bottle 2 conveyed at a high speed is efficiently cooled and quickly sets, and thus, the buckling 2c is prevented from occurring. In addition, since the nozzle openings on the opposite sides of the conveyance line of the bottle 2 are directed diagonally upward to the bottom 2b of the bottle 2 in such a manner that the extensions of the nozzle openings intersect with the conveyance line of the bottle 2, even when the coolant F is a liquid, such as water, droplets of the liquid are less likely to reach the mouth portion 2a of the bottle 2, so that the possibility of entry of the droplets to the bottle 2 is eliminated.

Figure 3:
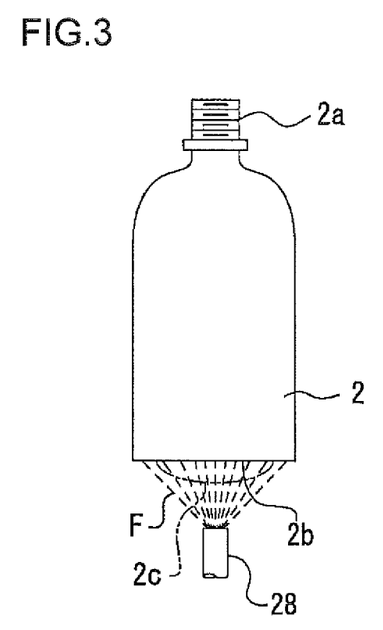
FIG. 3 is a diagram for illustrating a modification of a cooling step.

When the coolant F is a gas, such as air, as shown in FIG. 3, the gas as the coolant F may be injected from the nozzle opening of the coolant injection nozzle 28 directly opposed to the bottom 2b of the bottle 2. If the coolant F is a gas, the possibility that the coolant F injected from the nozzle opening enters the bottle 2 is low, and if the coolant F is air, the coolant F is harmless even if the coolant F enters the bottle 2. The cooling with a gas can also prevent occurrence of the buckling 2c.

After the bottom 2b of the bottle 2 has adequately set through the cooling step shown in FIG. 2(D), the bottle 2 is filled with a carbonated drink "a" from a filling nozzle 10 as shown in FIG. 2(E) and then capped with a cap 3 serving as a lid as shown in FIG. 2(F). Thus, occurrence of the buckling 2c on the bottom 2b of the bottle 2 is prevented with reliability. Since no buckling 2c occurs on the bottom 2b of the bottle 2, the bottled carbonated drink "a" product does not tilt or fall and is stored or exhibited in a stable posture, for example.

A carbonated drink filling system that performs the carbonated drink filling method is configured as shown in FIG. 4, for example.

As shown in FIG. 4, the carbonated drink filling system includes a preform supplying machine 11 (see FIG. 1(A)) that successively supplies preforms 1 having the shape of a bottomed tube having the mouth portion 2a at predetermined intervals, a blow molding machine 12 (see FIGS. 1(B) and 1(C)) that molds the preforms 1 into bottles 2, a cooling machine 29 (see FIG. 2(D)) that forcedly cools the bottoms 2b of the molded bottles 2, and a filling machine 13 (see FIGS. 2(E) and 2(F)) that fills the cooled bottles 2 with the drink "a" and seals the same with the caps 3.

The blow molding machine 12 and the filling machine 13 of the carbonated drink filling system are surrounded by chambers 41a and 41b. The chamber 41a may not be a sealed structure but be a simple frame structure such as a shroud.

Between the preform supplying machine 11 and the filling machine 13, a first conveying path for conveying the preform 1 or the like, a second conveying path for conveying the die 4 (see FIG. 1(C)) having the cavity C having the shape of the finished bottle 2, and a third conveying path for conveying the bottle 2 or the like molded in the die 4 are provided. The first to third conveying paths are coupled to each other, and a gripper (not shown) or the like that holds the preform 1 or bottle 2 during conveyance thereof is provided on these conveying paths.

In the preform supplying machine 11, the first conveying path includes a preform conveyor 14 that successively supplies the preforms 1 at predetermined intervals. In addition, the first conveying path is provided with a train of wheels 15, 16 and 17 that receives and conveys the preforms 1 from a terminal end of the preform conveyor 14 and an endless chain 18 that receives and conveys the preform 1.

The endless chain 18 is arranged as a conveying path for the preforms 1 in a heating furnace 33 provided with the infrared heater 18a described above. A large number of spindles 43 shown in FIG. 1(B) are attached to the endless chain 18 at regular intervals. Each spindle 43 can rotate on its axis while being transferred as the endless chain 18 travels. The spindle 43 is inserted into the mouth portion 2a of the preform 1 fed to the endless chain 18 from the wheel 17 as shown in FIG. 1(B), and thus, the preform 1 is held in the upright position on the spindle 43. If the mandrel is used instead of the spindle 43, the preform 1 can be supported and conveyed in the inverted position.

The heating furnace 33 has a furnace chamber extending in one direction. In the furnace chamber, the endless chain 18 is stretched between a pair of pulleys 34a and 34b opposed to each other in a horizontal plane. The endless chain 18 and associated members constitute an endless conveyor that conveys a large number of preforms 1 suspended. Infrared heaters 18a are attached to the inner wall surface of the furnace chamber along a going path and a return path of the endless chain 18.

Once the spindle 43 receives the preform 1 having been conveyed by the preform conveyor 14 and the train of wheels 15, 16 and 17, the preform 1 is transferred along the inner wall surface of the heating furnace 33 and is heated by the infrared heaters 18a. While the preform 1 is being transferred in the heating furnace 33, the preform 1 rotates on its axis as the spindle 43 rotates and is uniformly heated by the infrared heaters 18a until the temperature of the preform 1 excluding the mouth portion 2a rises to a temperature between 90° C. to 130° C. that is suitable for blow molding. The mouth portion 2a is kept at a temperature equal to or lower than 70° C. at which no deformation or the like occurs, in order to avoid compromising the sealing of the mouth portion 2a with the cap 3.

The blow molding machine 12 includes a plurality of sets of die 4 and extension rod 5 (see FIG. 1(C)) that receive the preforms 1 heated by the infrared heaters 18a in the preform supplying machine 11 described above and molds the preforms 1 into the bottles 2.

The second conveying path that conveys the preforms 1, the dies 4 and the bottles 2 passes through the blow molding machine 12. The second conveying path includes a train of wheels 19, 20, 21 and 22.

A plurality of dies 4 and a plurality of extension rods 5 are arranged around the wheel 20 and rotate at a constant speed around the wheel 20 as the wheel 20 rotates.

When the gripper (not shown) on the wheel 19 having received the preform 1 heated in the heating furnace 33 of the preform supplying machine 11 passes the preform 1 to the die 4 around the wheel 20, the die 4, which has been opened in two halves, is closed to hold the preform 1 as shown in FIG. 1(C). While the preform 1 in the die 4 is rotating around the wheel 20 together with the die 4 and the extension rod 5, high-pressure air for blow molding is blown from a blow nozzle (not shown) to mold the preform 1 into the bottle 2. The preform 1 is smoothly blow-molded, since the preform 1 has been uniformly heated to a predetermined temperature in the heating furnace 33 as shown in FIG. 1(B).

The preform 1 comes into close contact with the inner surface of the cavity C of the die 4 and is molded into the bottle 2. When the die 4 reaches the wheel 21, the die 4 is opened, and the bottle 2 is received by a gripper (not shown) on the wheel 21. The bottle 2 is conveyed to around the wheels 22 and 23.

The filling machine 13 has the third conveying path arranged therein, and the third conveying path includes a train of wheels 23, 24, 25, 26 and 27.

A large number of filling nozzles 10 that fills the bottles 2 with the drink "a" is arranged around the wheel 24 to form a filler 39, and a capper 40 that attaches the cap 3 (see FIG. 2(F)) to each bottle 2 filled with the drink "a" to seal the bottle 2 is formed around the wheel 26.

A train of wheels 21, 22 and 23 is interposed between the blow molding machine 12 and the filler 39 in the filling machine 13, and a large number of coolant injection nozzles 28 is arranged on the opposite sides of the bottles 2 conveyed by the train of wheels 21, 22 and 23. The arrangement of the coolant injection nozzles 28, the orientation of the nozzle openings and the like are as described above.

The bottle 2 having exited the blow molding machine 12 is transferred in the upright position between the rows of the coolant injection nozzles 28, and the coolant F is blasted to the bottom 2b as shown in FIG. 2(D) to cool the bottle 2 to a temperature at which the entire bottle 2 including the bottom 2b is not easily deformed until the bottle 2 reaches the filler 39 in the filling machine 13.

Upon reaching the filler 39, the cooled bottle 2 is filled with the carbonated drink "a" from the filling nozzle 10 as shown in FIG. 2(E), and the mouth portion 2a of the bottle 2 is sealed with the cap 3 by the capper 40. In particular, when the bottle 2 is filled with the carbonated drink, the bottom 2b of the bottle 2 is adequately cooled and has set, no buckling 2c occurs on the bottom 2b of the bottle 2 when the mouth portion 2a of the bottle 2 is sealed with the cap 3.

Next, a series of operations of the carbonated drink filling system will be described.

First, the preform 1 is conveyed toward the heating furnace 33 by the preform conveyor 14 and the train of wheels 15, 16 and 17.

The preform 1 is received by the spindle 43 (see FIG. 1(B)) on the endless chain 18 and conveyed into the heating furnace 33.

In the heating furnace 33, the preform 1 is uniformly heated by the infrared heaters 18a until the temperature of the preform 1 excluding the mouth portion 2a reaches a temperature range suitable for blow molding.

The preform 1 heated to a molding temperature in the heating furnace 33 is held by the die 4 as shown in FIG. 1(C) and passes by the outer circumference of the wheel 20, and high-pressure air is blasted into the preform 1 from a blow nozzle (not shown) in the vicinity of the extension rod 5, thereby expanding the preform 1 in the cavity C to form the bottle 2 as the finished product.

The molded bottle 2 is removed from the die 4 by the gripper on the wheel 21 after the die 4 is opened, and conveyed on the conveying path formed by the train of wheels 21, 22 and 23.

The coolant F, such as water, is injected to the bottom 2b of the bottle 2 from the coolant injection nozzles 28 on the opposite sides of the bottle 2 being conveyed by the train of wheels 21, 22 and 23. As a result, in particular, the bottom 2b of the bottle 2 is intensively cooled and hardens.

In the filling machine 13, the bottle 2 is filled with the carbonated drink "a" from the filling nozzle 10 of the filler 39 as shown in FIG. 2(E). Although high pressure is applied to the interior of the bottle 2 when the bottle 2 is filled with the carbonated drink "a", the bottle 2 including the bottom 2b, which is the thickest part, has adequately set at this point in time, so that the buckling 2c or other deformation does not occur on the bottom 2b.

The bottle 2 filled with the drink "a" is sealed with the cap 3 by the capper 40 (see FIG. 2(F)) and discharged from an outlet port of the chamber 41b.

Second Embodiment

Figure 5:
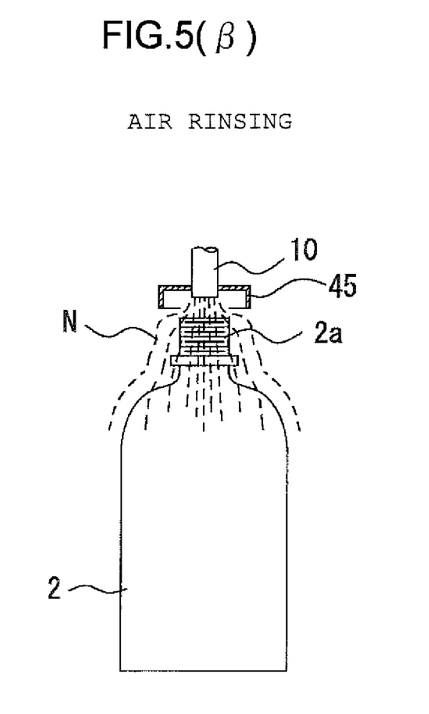
FIG. 5 is a diagram for illustrating a sterilization step additionally provided in a second embodiment of the present invention.

According to a second embodiment, a step of sterilizing the bottle 2 shown in FIGS. 5($\alpha$) and 5($\beta$) is performed between the step of cooling the bottom 2b of the bottle 2 shown in FIG. 2(D) and the step of filling the bottle 2 with the carbonated drink "a" shown in FIG. 2(E).

Specifically, as shown in FIG. 5(α), a mist M or gas G of hydrogen peroxide is blasted to the bottle 2 whose bottom 2b has been cooled and set to an extent that no buckling 2c occurs. More specifically, while the bottle 2 is being conveyed in the upright position with the mouth portion 2a thereof facing up, a spray nozzle 6 arranged at a fixed position injects the mist M or gas G of hydrogen peroxide to the mouth portion 2a of the bottle 2 from directly above the mouth portion 2a. The injected mist M or gas G flows into the bottle 2 or spills from the bottle 2 to flow down along the outer surface of the bottle 2. In this way, a uniform coating of hydrogen peroxide is deposited on the inner and outer surfaces of the bottle 2.

As shown in FIG. 5(β), heated air N is then blasted to the bottle 2. Specifically, while the bottle 2 is being conveyed in the upright position, an air nozzle 10 arranged at a fixed position injects the heated air N to the mouth portion 2a of the bottle 2 from directly above the mouth portion 2a. The injected heated air N flows into the bottle 2 or spills from the bottle 2 to flow down along the outer surface of the bottle 2. As a result of the supply of the heated air N, the hydrogen peroxide deposited on the inner and outer surfaces of the bottle 2 is heated and activated, and the effect of sterilization of the inner and outer surfaces of the bottle 2 is improved. In addition, an excess of the hydrogen peroxide is discharged from the bottle 2.

As shown in FIGS. 5(α) and 5(β), the hydrogen peroxide spray nozzle 6 and the air-rinsing air nozzle 10 are each provided with an umbrella-shaped guide member 45 at a tip end thereof. The mist M or gas G of hydrogen peroxide injected from the spray nozzle 6 and the heated air N injected from the air-rinsing air nozzle 10 are guided by the respective guide members 45 to flow along the thread on the outside of the mouth portion 2a of the bottle 2. As a result, the outer surface of the bottle 2 including the mouth portion 2a is efficiently sterilized. The guide members 45 are provided as required to achieve efficient sterilization of the outer surface of the mouth portion 2a.

The bottle 2 thus sterilized is filled with the carbonated drink "a" as shown in FIG. 2(E) and sealed with the cap 3 as shown in FIG. 2(F).

Figure 6:
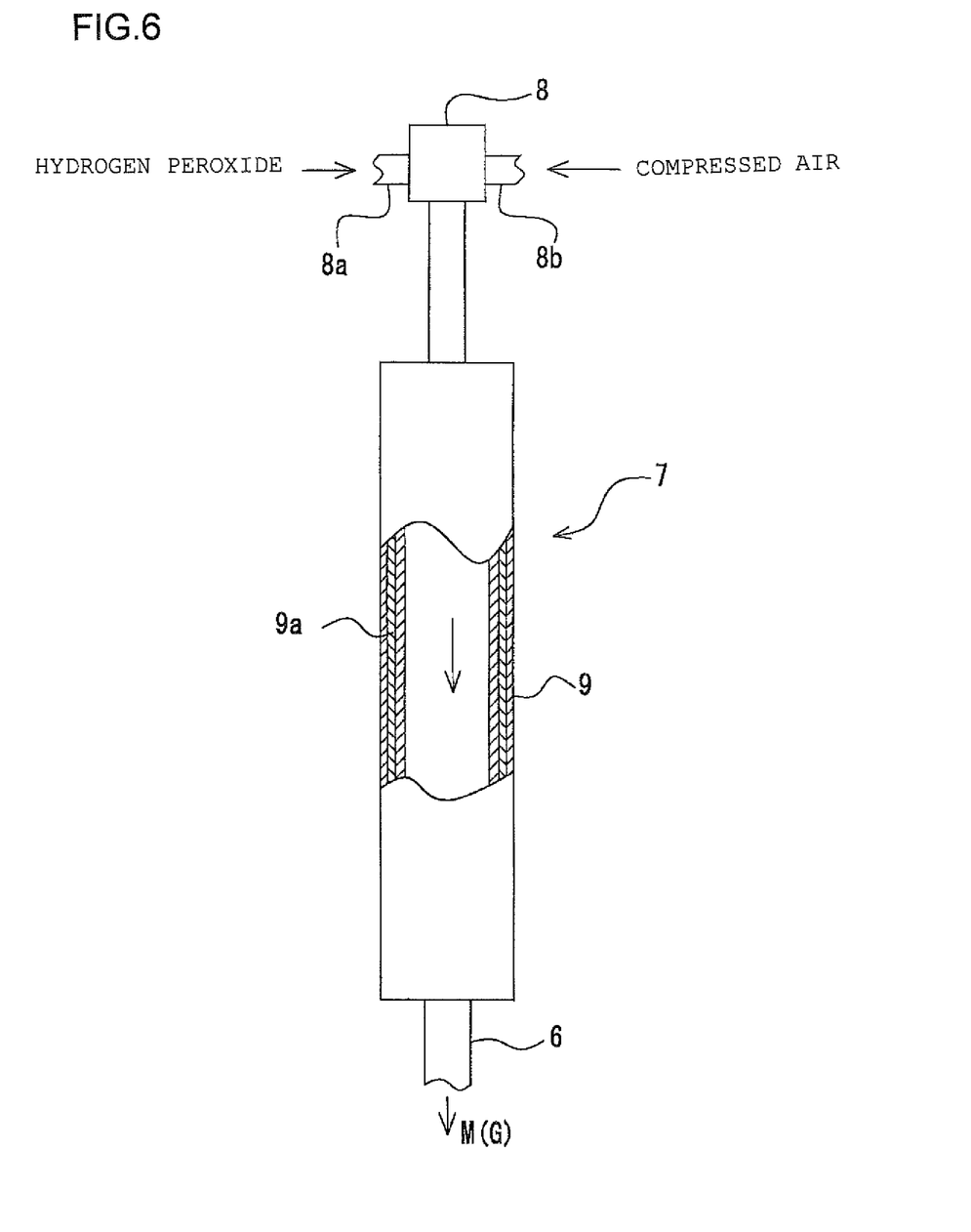
FIG. 6 is a partially cut-away view of a hydrogen peroxide mist generator.

The mist M or gas G of hydrogen peroxide described above is generated by a mist generator 7 shown in FIG. 6.

The mist generator 7 includes a hydrogen peroxide supplying portion 8 that is a twin-fluid spray nozzle that supplies a hydrogen peroxide solution serving as a sterilizer in the form of drops and an evaporating portion 9 that evaporates a spray of hydrogen peroxide supplied from the hydrogen peroxide supplying portion 8 by heating the spray of hydrogen peroxide to a temperature equal to or higher than the boiling point thereof and equal to or lower than the non-degradable temperature thereof. The hydrogen peroxide supplying portion 8 is configured to receive the hydrogen peroxide solution and compressed air from a hydrogen peroxide supply path 8a and a compressed air supply path 8b, respectively, and sprays the hydrogen peroxide solution into the evaporating portion 9. The evaporating portion 9 is a pipe that incorporates a heater 9a disposed between inner and outer walls thereof, and heats and evaporates the spray of hydrogen peroxide blasted into the pipe. The spray nozzle 6 described above is arranged at the end of the evaporating portion 9 opposite to the hydrogen peroxide supplying portion 8. The gas of hydrogen peroxide produced by the evaporating portion 9 is injected from the spray nozzle 6 in the form of the mist M or gas G. Thus, the hydrogen peroxide is uniformly deposited on the inner and outer surfaces of the bottle 2.

Figure 7:
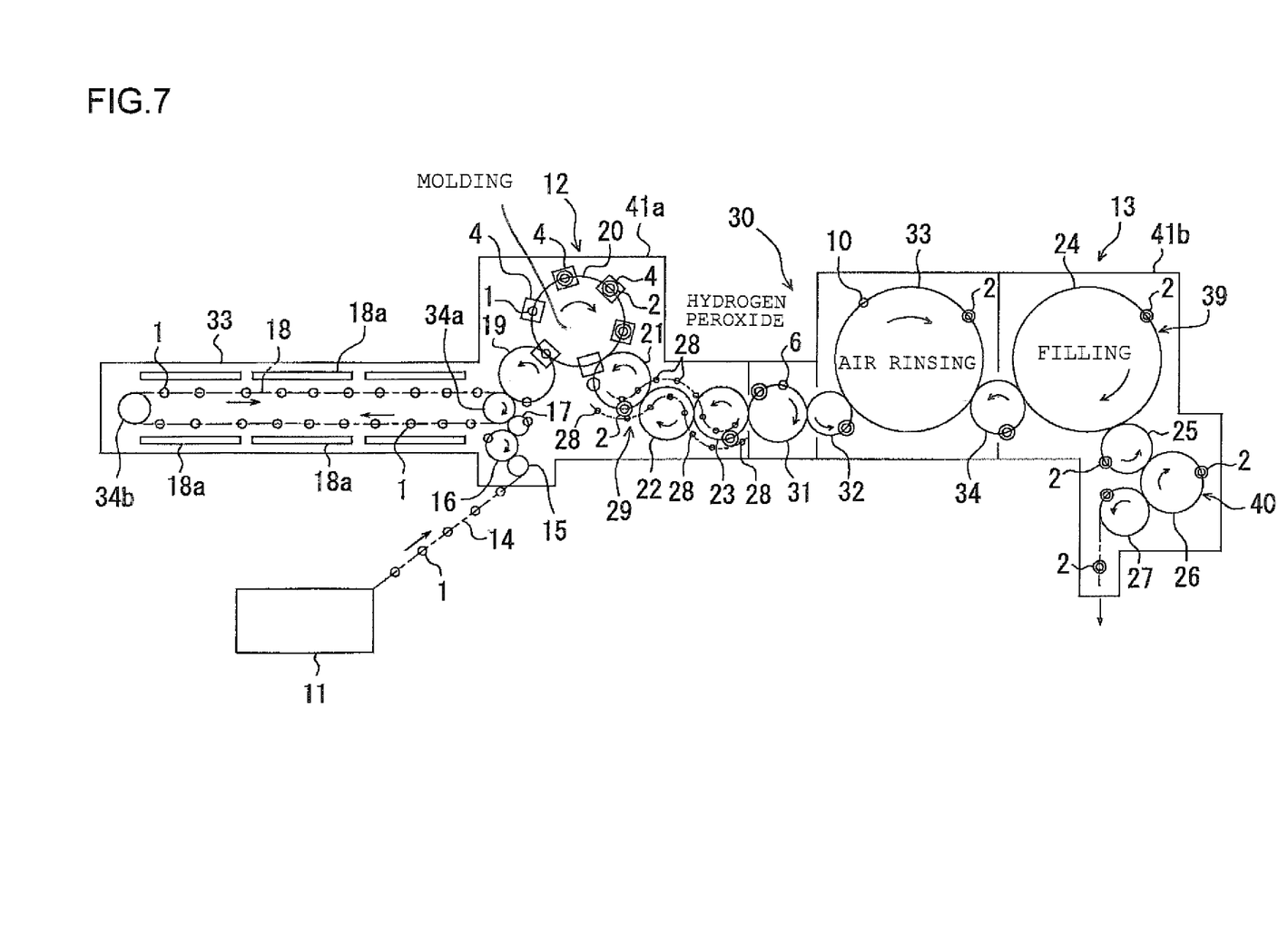
FIG. 7 is a schematic plan view of a carbonated drink filing system according to the second embodiment of the present invention.

A carbonated drink filling system that performs the carbonated drink filling method according to the second embodiment is configured as shown in FIG. 7, for example. The carbonated drink filling system includes the preform supplying machine 11 (see FIG. 1(A)) that successively supplies preforms 1 at predetermined intervals, the blow molding machine 12 (see FIGS. 1(B) and 1(C)) that molds the preforms 1 into the bottles 2, the cooling machine 29 (see FIG. 2(D)) that forcedly cools the bottoms of the molded bottles 2, a sterilizing machine 30 (see FIGS. 5(α) and 5(β)) that sterilizes the cooled bottles 2, and the filling machine 13 (see FIGS. 2(E) and 2(F)) that fills the sterilized bottles 2 with the carbonated drink "a" and seals the same with the caps 3.

To provide the sterilizing machine 30 in the carbonated drink filling system, unlike the first embodiment, a train of wheels 31, 32, 33 and 34 is additionally provided between the last wheel 23 in the cooling machine 29 and the wheel 24 in the filler 39. The spray nozzle 6 described above is arranged around the wheel 31, and the air nozzle 10 described above is arranged around the wheel 33.

With the carbonated drink filling system, after the bottom 2b of the bottle 2 is cooled to prevent occurrence of the buckling 2c, the mist M or gas G of hydrogen peroxide and the heated air N are supplied to sterilize the bottle 2, and the bottle 2 is then filled with the carbonated drink "a". At the time when the bottle 2 is filled with the carbonated drink "a", the bottom 2b of the bottle 2 has been cooled and set, so that no buckling 2c occurs on the bottom 2b of the bottle 2 even though the carbonated drink "a" applies pressure to the interior of the bottle 2.

Third Embodiment

Figure 8:
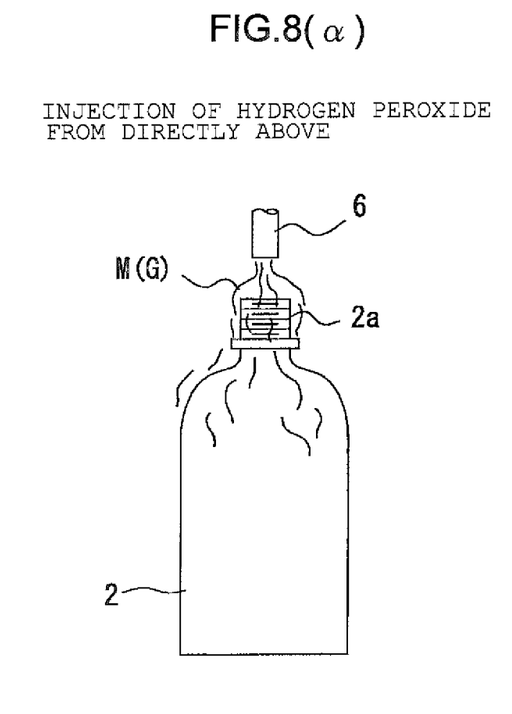
FIG. 8 is a diagram for illustrating a sterilization step and a cooling step additionally provided in a third embodiment of the present invention.

According to a third embodiment, a step of sterilizing the bottle 2 shown in FIGS. 8(α) and 8(β) and a second step of cooling the bottom 2b of the bottle 2 shown in FIG. 8(D1) are performed between the step of cooling the bottom 2b of the bottle 2 shown in FIG. 2(D) and the step of filling the bottle 2 with the carbonated drink "a" shown in FIG. 2(E).

According to the third embodiment, the bottom 2b of the bottle 2 is cooled in two steps before and after the sterilization step, and thus, the degree of cooling in the first cooling step shown in FIG. 2(D) can be lower than the degree of cooling in the cooling step according to the second embodiment. That is, the flow rate of the coolant F used in the first cooling step can be reduced, or the number of coolant injection nozzles 28 installed can be reduced.

In this case also, the bottom 2b of the bottle 2 is cooled to an extent that no buckling 2c occurs. In addition, since the sterilization step shown in FIGS. 8(α) and 8(β) is performed on the bottle 2 that has more residual heat than in the second embodiment, the effect of sterilization in the sterilization step is improved.

After the sterilization step, the second cooling step is performed as shown in FIG. 8(D1) to further cool the bottom 2b of the bottle 2, so that occurrence of the buckling 2c is completely prevented.

Furthermore, since the first cooling step is performed before sterilization, there is no need to use aseptic air, aseptic water or a chemical agent, and inexpensive means, such as compressed air from a compressor or air from a blower, will suffice. However, in the second cooling step, aseptic air, aseptic water or a chemical agent needs to be used.

The sterilized and cooled bottle 2 is filled with the carbonated drink "a" as shown in FIG. 2(E) and then capped as shown in FIG. 2(F).

Figure 9:
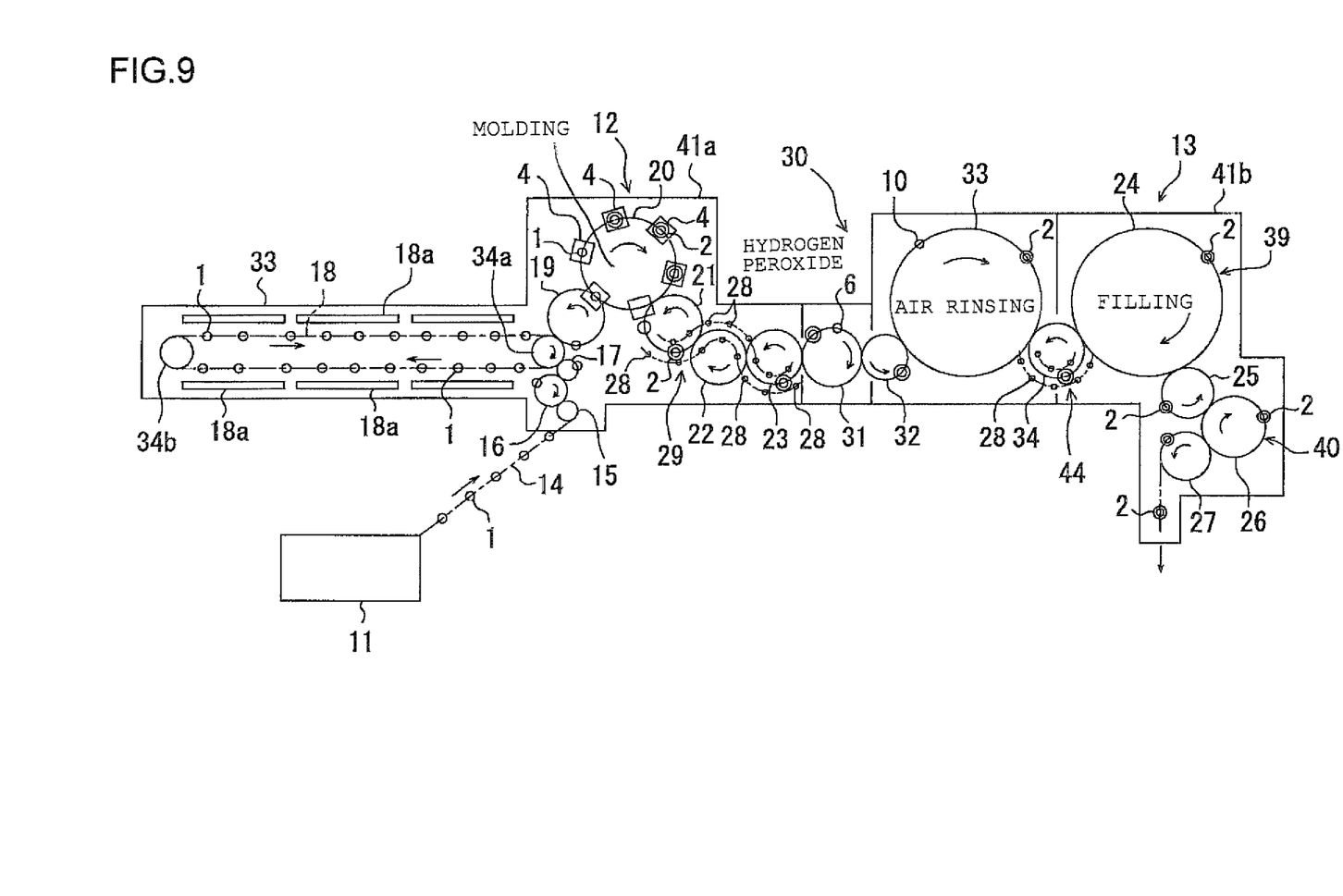
FIG. 9 is a schematic plan view of a carbonated drink filing system according to a third embodiment of the present invention.

A carbonated drink filling system that performs the carbonated drink filling method according to the third embodiment is configured as shown in FIG. 9, for example. The carbonated drink filling system includes the preform supplying machine 11 (see FIG. 1(A)) that successively supplies preforms 1 at predetermined intervals, the blow molding machine 12 (see FIGS. 1(B) and 1(C)) that molds the preforms 1 into the bottles 2, a first-stage cooling machine 29 (see FIG. 2(D)) that forcedly cools the bottoms 2b of the molded bottles 2, the sterilizing machine 30 (see FIGS. 8(α) and 8(β)) that sterilizes the cooled bottles 2, a second-stage cooling machine 44 (see FIG. 8(D1)) that forcedly further cools the bottoms 2b of the sterilized bottles 2, and the filling machine 13 (see FIGS. 2(E) and 2(F)) that fills the sterilized and cooled bottles 2 with the drink "a" and seals the same with the caps 3.

To provide the first-stage cooling machine 29 and the second-stage cooling machine 44 in the carbonated drink filling system, unlike the second embodiment, the coolant injection nozzles 28 according to the second embodiment are divided into two groups, and each of the cooling machines 29 and 44 includes one of the groups of coolant injection nozzles 28, for example.

With the carbonated drink filling system, after the bottom 2b of the bottle 2 is cooled to some extent, the mist M or gas G of hydrogen peroxide and the heated air N are supplied to sterilize the bottle 2. After that, the bottom 2b of the bottle 2 is cooled to an extent that no buckling 2c occurs on the bottom 2b of the bottle 2, and the bottle 2 is then filled with the carbonated drink "a".

Fourth Embodiment

According to a fourth embodiment, the step of sterilizing the bottle 2 shown in FIGS. 5(α) and 5(β) is performed between the step of molding the bottle 2 shown in FIG. 1(C) and the step of cooling the bottom 2b of the bottle 2 shown in FIG. 2(D).

Specifically, a mist M or gas G of hydrogen peroxide is blasted to the bottle 2 having just been removed from the molding die 4 as shown in FIG. 5(α), heated air N is then blasted to the bottle 2 as shown in FIG. 5(β), and the bottom 2b of the bottle 2 is then forcedly cooled as shown in FIG. 2(D).

Most of the heat applied to the preform 1 remains in the bottle 2 having just been removed from the molding die 4, and the residual heat activates the hydrogen peroxide and improves the sterilization effect.

After the sterilization process of the bottle 2, the step of cooling the bottom 2b of the bottle 2 shown in FIG. 2(D) is performed to cool the bottom 2b of the bottle 2, thereby making the bottom 2b harden so that no buckling 2c occurs.

The sterilized and cooled bottle 2 is filled with the carbonated drink "a" as shown in FIG. 2(E) and then capped as shown in FIG. 2(F).

Figure 10:
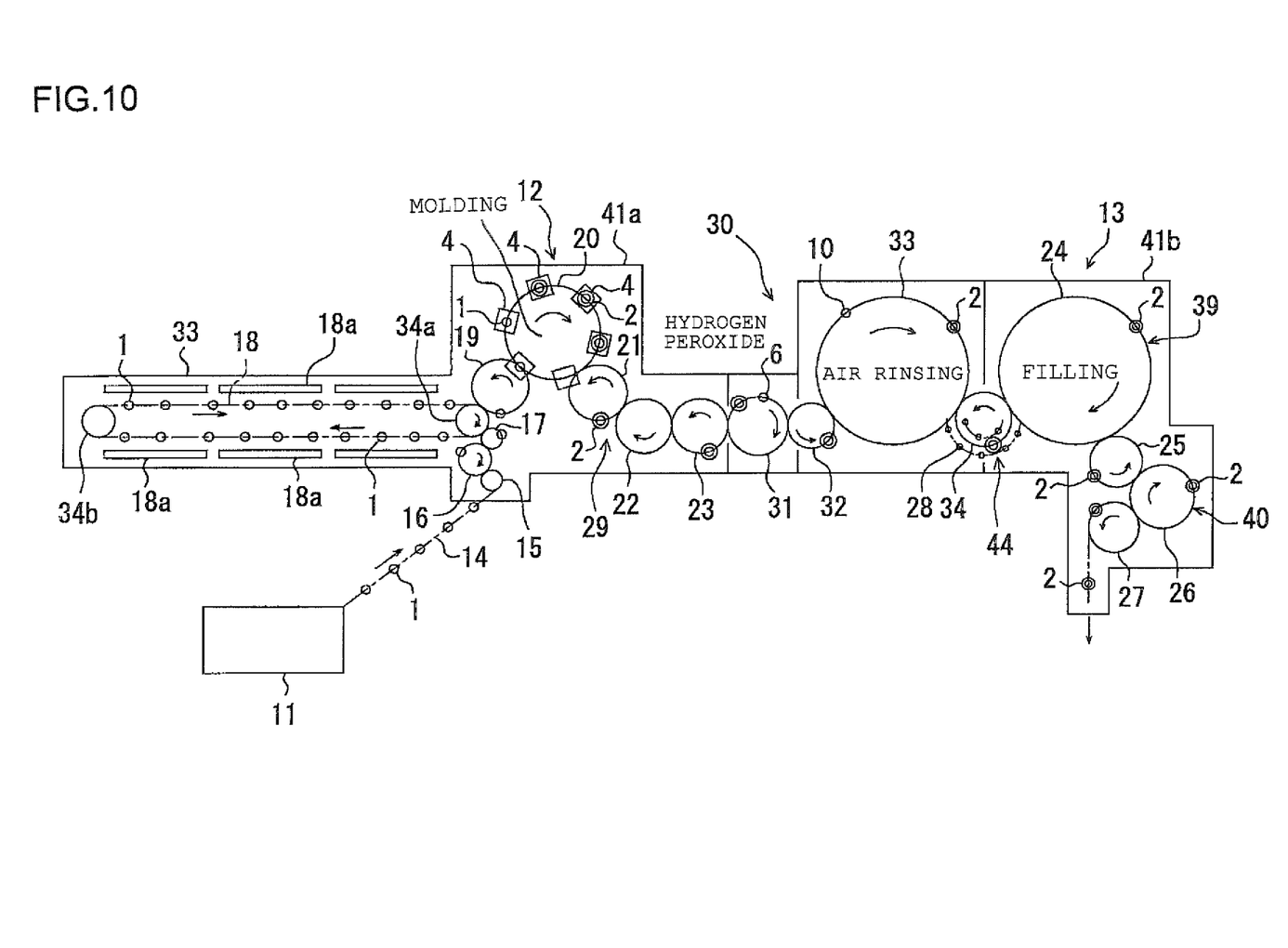
FIG. 10 is a schematic plan view of a carbonated drink filing system according to a fourth embodiment of the present invention.

A carbonated drink filling system that performs the carbonated drink filling method according to the fourth embodiment is configured as shown in FIG. 10, for example.

Specifically, the carbonated drink filling system includes the preform supplying machine 11 (see FIG. 1(A)) that successively supplies preforms 1 at predetermined intervals, the blow molding machine 12 (see FIGS. 1(B) and 1(C)) that molds the preforms 1 into the bottles 2, the sterilizing machine 30 (see FIGS. 5(α) and 5(β)) that sterilizes the molded bottles 2, a cooling machine 44 (see FIG. 2(D)) that forcedly cools the bottoms 2b of the sterilized bottles 2, and the filling machine 13 (see FIGS. 2(E) and 2(F)) that fills the sterilized bottles 2 with the carbonated drink "a" and seals the same with the caps 3.

Unlike the second embodiment, the cooling machine 28 is displaced to between the sterilizing machine 30 and the filler 39 and denoted by reference numeral 44.

With the carbonated drink filling system, the molded bottle 2 is sterilized when the bottle 2 is still hot. After that, the bottom 2b of the bottle 2 is cooled so that no buckling 2c occurs, and the bottle 2 is then filled with the carbonated drink "a".

Fifth Embodiment

Figure 11:
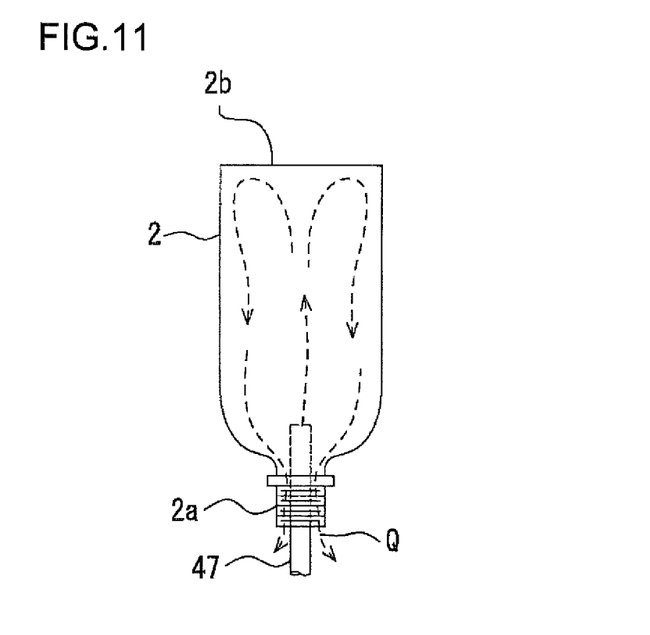
FIG. 11 is a diagram for illustrating a water rinsing step additionally provided in a fifth embodiment of the present invention.

According to a fifth embodiment, the step of sterilizing the bottle 2 shown in FIGS. 5(α) and 5(β) and a water rinsing step shown in FIG. 11 are performed between the step of molding the bottle 2 shown in FIG. 1(C) and the step of cooling the bottom 2b of the bottle 2 shown in FIG. 2(D).

Specifically, a mist M or gas G of hydrogen peroxide is blasted to the bottle 2 having just been removed from the molding die 4 (see FIG. 10) as shown in FIG. 5(α), heated air N is then blasted to the bottle 2 as shown in FIG. 5(β), the bottle 2 is inverted and rinsed with water by injecting aseptic water Q into the bottle 2 in the inverted position from a nozzle 47 as shown in FIG. 11, and the bottom 2b of the bottle 2 restored to the upright position is then forcedly cooled as shown in FIG. 2(D).

Most of the heat applied to the preform 1 remains in the bottle 2 having just been removed from the molding die 4, and the residual heat activates the hydrogen peroxide deposited on the bottle 2 and improves the sterilization effect.

After the sterilization process of the bottle 2, the heated air N is blasted to the bottle 2, thereby activating the hydrogen peroxide, improving the sterilization effect, and removing an excess of the hydrogen peroxide on the surface of the bottle 2. After that, water rinsing of the bottle 2 is performed in the inverted position with the mouth portion 2a facing down, thereby washing the interior of the bottle 2 with the aseptic water Q to remove foreign matters from the interior of the bottle 2. The aseptic water Q used for the water rinsing forcedly cools the bottom 2b of the bottle 2 from inside the bottle 2.

The air rinsing shown in FIG. 5(β) in the sterilization step may be replaced with the water rinsing and omitted.

After the water rinsing of the bottle 2, the step of cooling the bottom 2b of the bottle 2 restored to the upright position is performed as shown in FIG. 2(D). Thus, the bottom 2b of the bottle 2 is cooled to harden so that no buckling 2c occurs. In addition to being cooled by the water rinsing, the bottom 2b of the bottle 2 is further cooled by the coolant F injected from the coolant injection nozzles 28, so that occurrence of the buckling 2c on the bottom 2b of the bottle 2 is more effectively prevented.

The bottle 2 thus sterilized, rinsed with water and cooled is filled with the carbonated drink "a" as shown in FIG. 2(E) and then capped as shown in FIG. 2(F).

Figure 12:
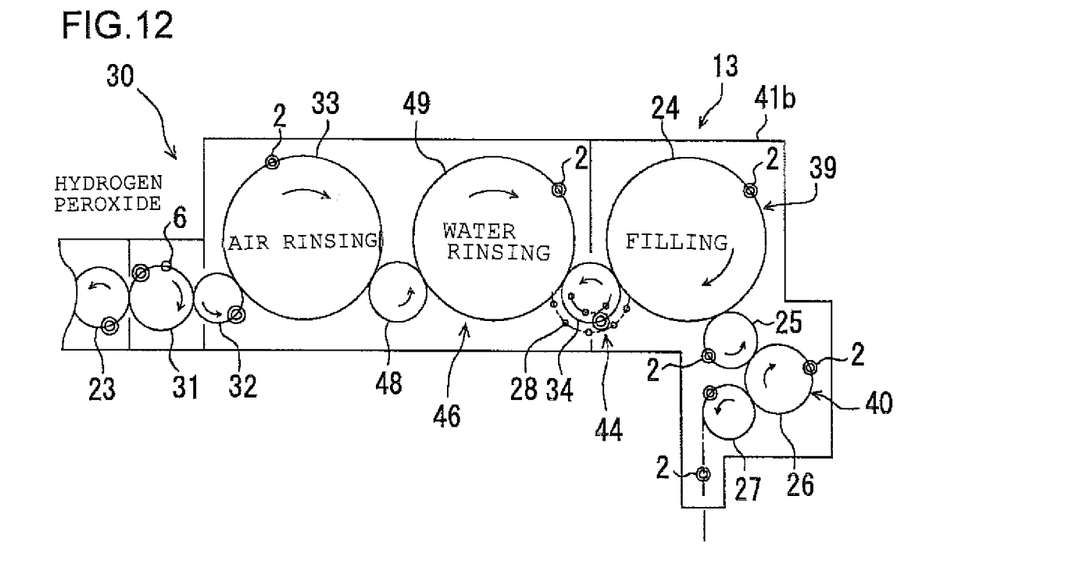
FIG. 12 is a partially cut-away schematic plan view of a carbonated drink filling system according to the fifth embodiment of the present invention.

A carbonated drink filling system that performs the carbonated drink filling method according to the fifth embodiment is configured as shown in FIG. 12, for example.

Specifically, the carbonated drink filling system includes the preform supplying machine 11 (see FIG. 1(A)) that successively supplies preforms 1 at predetermined intervals, the blow molding machine 12 (see FIGS. 1(B) and 1(C)) that molds the preforms 1 into the bottles 2, the sterilizing machine 30 (see FIGS. 5(α) and 5(P)) that sterilizes the molded bottles 2, a water rinsing machine 46 (see FIG. 11)

that rinses the bottles 2 with water, the cooling machine 44 (see FIG. 2(D)) that forcedly cools the bottoms 2*b* of the bottles 2 rinsed with water, and the filling machine 13 (see FIGS. 2(E) and 2(F)) that fills the cooled bottles 2 with the carbonated drink "a" and seals the same with the caps 3.

As shown in FIG. 12, since the water rinsing machine 46 is additionally provided, wheels 48 and 49 are added to the carbonated drink filing system according to the fourth embodiment shown in FIG. 10.

With the carbonated drink filling system, the molded bottle 2 is sterilized when the bottle 2 is still hot. After that, the bottle 2 is washed, the bottom 2*b* of the bottle 2 is cooled so that no buckling 2*c* occurs, and the bottle 2 is then filled with the carbonated drink "a".

When the bottle is made of PET, the temperature of the rinsing water can be any temperature that is equal to or lower than the glass transition temperature thereof (specifically, equal to or lower than 75° C.). The rinsing water desirably comes into contact with at least a central part (gate part) of the bottom of the interior of the bottle. The duration of the rinsing is desirably equal to or longer than at least 0.2 seconds. As far as the temperature of the rinsing liquid is equal to or lower than 75° C., the rinsing liquid is not limited to the aseptic water, and any liquid having a sterilization effect, such as peracetic acid, hot water, an alkali solution, acid water, ozone water or chlorine water, has the same cooling effect. The level of sterilization of the container can be any level equal to or higher than the required level of sterilization for the content of the bottle, which is the carbonated drink. Thus, in the case of an unsterilized carbonated drink, unsterilized water can also be used.

The present invention is not limited to the embodiments described above, and various modifications can be made to the embodiments. For example, although a dry sterilization process using hydrogen peroxide is used to sterilize the bottle in the embodiments described above, a wet (rinsing) sterilization process using a liquid such as water may be used to sterilize the bottle. Alternatively, the bottle may be sterilized by irradiating the bottle with an electron beam or ultraviolet rays.

REFERENCE SIGNS LIST

1 preform
2 bottle
2*a* mouth portion of bottle
2*b* bottom of bottle
4 molding die
28 coolant injection nozzle
30 sterilizing machine
33 heating furnace
39 filler
40 capper
F coolant
a carbonated drink

The invention claimed is:

1. A carbonated drink filling method, comprising the steps of:
   transferring a preform continuously,
   introducing the preform into a heating furnace,
   heating the preform to a temperature for molding the preform into a container in the heating furnace,
   molding the heated preform into the container in a molding die after the preform exits the heating furnace,
   conveying the container in an upright position,
   applying a first coolant to a bottom of the container to cool the bottom of the container, the first coolant being applied to the bottom of the container from a nozzle opening on either or both sides of a conveyance line of the container, and a centerline of the nozzle opening is directed diagonally upward to the bottom of the container in such a manner that an extension of the nozzle opening intersects with the conveyance line of the container,
   sterilizing the container after applying the first coolant and before the container is filled with a carbonated drink,
   applying a second coolant to the bottom of the container after the sterilizing of the container,
   filling the container with the carbonated drink through a mouth portion of the container, and
   sealing the mouth portion of the container.

2. The carbonated drink filling method according to claim 1, the method further comprising the steps of:
   water rinsing the container after the sterilizing of the container, and
   applying the second coolant to the bottom of the container after the water rinsing.

3. A carbonated drink filling system, comprising:
   a transfer device that transfers a preform from where the preform is supplied and molded into a container, and that transfers the container from where the container is filled with a carbonated drink and sealed;
   a heating furnace that heats the preform to a molding temperature;
   a blow molding device that blow-molds the preform into the container;
   a first coolant applying nozzle that applies a first coolant to a bottom of the container discharged from a blow molding die in an upright position to cool the bottom of the container, the first coolant applying nozzle being provided on either or both sides of a conveyance line which the container moves along, and the first coolant applying nozzle applying the first coolant from a nozzle opening, such that a centerline of the nozzle opening is directed diagonally upward to the bottom of the container in such a manner that an extension of the nozzle opening intersects with the conveyance line of the container;
   a sterilization device which performs a sterilization process on the container, is provided downstream of the first coolant applying nozzle
   a second coolant applying nozzle, which applies a second coolant to the bottom of the container after the sterilization process on the container, is provided downstream of the sterilization device,
   a filler that fills the container with the carbonated drink through a mouth portion of the container; and
   a capper that seals the mouth portion of the container,
   wherein the heating furnace, the blow molding device, the first coolant applying nozzle, the sterilization device, the second coolant applying nozzle, the filler and the capper are arranged in this order from an upstream side to a downstream side, with the first coolant applying nozzle and the second coolant applying nozzle being along the transfer device.

4. The carbonated drink filling system according to claim 3, wherein a water rinsing device is provided downstream of the sterilization device, and the second coolant applying nozzle is provided between the water rinsing device and the filler.

* * * * *